(12) United States Patent  
Schwarzberg et al.

(10) Patent No.: US 8,326,646 B2  
(45) Date of Patent: Dec. 4, 2012

(54) METHOD AND SYSTEM FOR SUGGESTING MEALS BASED ON TASTES AND PREFERENCES OF INDIVIDUAL USERS

(75) Inventors: Robert Schwarzberg, Boca Raton, FL (US); Marion Zabinski, San Diego, CA (US); Rene Melton, Delray Beach, FL (US); Timothy J. Dion, Parkland, FL (US)

(73) Assignee: Humana Innovations Enterprises, Inc., Louisville, KY (US)

( * ) Notice: Subject to any disclaimer, the term of this patent is extended or adjusted under 35 U.S.C. 154(b) by 721 days.

(21) Appl. No.: 12/117,820

(22) Filed: May 9, 2008

(65) Prior Publication Data

US 2009/0077007 A1    Mar. 19, 2009

Related U.S. Application Data

(63) Continuation-in-part of application No. 12/117,190, filed on May 8, 2008, which is a continuation-in-part of application No. 11/856,917, filed on Sep. 18, 2007.

(51) Int. Cl.  
*G06Q 10/00* (2012.01)
(52) U.S. Cl. .............................. 705/2; 705/3
(58) Field of Classification Search ............... 705/2  
See application file for complete search history.

(56) References Cited

U.S. PATENT DOCUMENTS

| | | | |
|---|---|---|---|
| 5,377,258 A | 12/1994 | Bro | |
| 5,673,691 A | 10/1997 | Abrams et al. | |
| 5,704,350 A * | 1/1998 | Williams, III | 600/300 |
| 5,832,448 A | 11/1998 | Brown | |
| 5,890,128 A | 3/1999 | Diaz et al. | |

(Continued)

FOREIGN PATENT DOCUMENTS

WO        9944494        9/1999

(Continued)

OTHER PUBLICATIONS

Be Well Mobile, A Picture of Health, Patient Engagement Software That Works, http://www.bewellmobile.com; http://www.bewellmobile.com/products-services.html; http://www.bewellmobile.com/biographies.html; http://www.bewellmobile.com/patient-engagement.html, 6 pages from website, Copyright 2006, Feb. 21, 2007.

(Continued)

*Primary Examiner* — Hiep V Nguyen  
(74) *Attorney, Agent, or Firm* — Standley Law Group LLP

(57) ABSTRACT

A system and method for generating meal suggestion messages using an expert system and then pushing those suggestions to users. Meal suggestions are tailored to users based on their tastes and preferences. Users specify preferences related to a diet plan, food preferences, meal time preferences, and meal preparation preferences. An expert system considers each user's preferences and nutritional data to generate meal suggestion messages consistent with the user's preferences and dietary goals. Meal suggestions are pushed to the user according to the user's preferred time for eating each meal. The user can accept or reject the suggested meal or one or more foods within a suggested meal. For rejected meal suggestions, a meal substitution message is generated and sent. The expert system uses accepted and rejected meal suggestions to determine if certain foods or entire meals should no longer be recommended to individual users or to system users as a whole.

18 Claims, 21 Drawing Sheets

U.S. PATENT DOCUMENTS

| | | | |
|---|---|---|---|
| 5,897,493 A | 4/1999 | Brown | |
| 5,954,510 A | 9/1999 | Merrill et al. | |
| 6,039,688 A | 3/2000 | Douglas et al. | |
| 6,246,992 B1 | 6/2001 | Brown | |
| 6,366,871 B1 | 4/2002 | Geva | |
| 6,602,191 B2 | 8/2003 | Quy | |
| 6,811,516 B1 | 11/2004 | Dugan | |
| 6,936,007 B2 | 8/2005 | Quy | |
| 6,968,375 B1 | 11/2005 | Brown | |
| 6,976,958 B2 | 12/2005 | Quy | |
| 6,980,999 B1 * | 12/2005 | Grana | 707/803 |
| 7,090,638 B2 | 8/2006 | Vidgen | |
| 7,156,809 B2 | 1/2007 | Quy | |
| 7,222,054 B2 | 5/2007 | Geva | |
| 2002/0128804 A1 | 9/2002 | Geva | |
| 2005/0021361 A1 | 1/2005 | Huang et al. | |
| 2005/0021372 A1 | 1/2005 | Mikkelsen et al. | |
| 2005/0113649 A1 | 5/2005 | Bergantino | |
| 2005/0113650 A1 | 5/2005 | Pacione et al. | |
| 2006/0041452 A1 | 2/2006 | Kulkarni | |
| 2006/0058586 A1 | 3/2006 | Humble | |
| 2006/0064447 A1 | 3/2006 | Malkov | |
| 2006/0178907 A1 | 8/2006 | Humble | |
| 2006/0189853 A1 | 8/2006 | Brown | |
| 2006/0199155 A1 | 9/2006 | Mosher | |
| 2006/0287883 A1 | 12/2006 | Turgiss et al. | |
| 2007/0021984 A1 | 1/2007 | Brown | |
| 2007/0030339 A1 | 2/2007 | Findlay et al. | |

FOREIGN PATENT DOCUMENTS

| | | |
|---|---|---|
| WO | 2006021956 | 3/2006 |
| WO | 2006138680 | 12/2006 |

OTHER PUBLICATIONS

BeWell Mobile Forms Partnership with Wipro for Disease Management, BeWell Also Named Finalist in Global Software Competition Conduct by Qualcomm, Press Release, Dec. 6, 2006.

Diet Tiny Assist, http://www.wimos.com/diet.html, 4 pages from website, Feb. 16, 2007.

Welcome to Health Hero Network, Making Connections for Life, Heath Buddy System, http://www.healthhero.com/products services/products services.html; http://www.healthhero.com/products services/peripherals.html, 4 pages from website, Copyright 2006, Feb. 12, 2007.

Palm OS, Keyoe, Software products to organize and enhance your life, http://www.keyoe.com/DEA Handheld.htm, 8 pages from website, Copyright 2000-2007, Last modified: Dec. 2, 2006, Feb. 16, 2007.

Card Guard AG and Humana form new company to provide innovative wireless platform for wellness and disease management, Press Release, Oct. 17, 2005.

Ali, Sarmad, Technology Enlisting cellphones to fight cellulite, The Wall Street Journal, http://www.post-gazette.com/pg/06236/716009-96.stm, Aug. 24, 2006.

Sensei, Changing Mindsets with Handsets, http://www.sensei.com, 1 page from website, Copyright 2005, Mar. 13, 2007.

Card Guard: Card Guard receives approval from Israeli Court to become Swiss-based, Press Release, 1 page from website, Oct. 23, 2001, http://www.cardguard.com/newsite/inner.asp?lang=1&newsid=43&type=1&cat=44.

* cited by examiner

HOME · WHY Sensei · ARTICLES · RECIPES · HEALTH TOOLS · FAQ · About Sensei · JOIN    MY Sensei.com (login)

*Sensei* CHANGING MINDSETS WITH HANDSETS

Your wellness starts now!

Gender  ○ Male  ● Female
Age  [47]
Weight  [140] Lb
Goal Weight  [130] Lb
Height  [5 ▾] Ft  [4 ▾] In

[ SEND > ]

200

Setting Your Goal Weight

Rome wasn't built in a day, and neither were you! It took a while to gain it, so cut yourself some slack when it's time to lose it. Instead of one BIG goal, set several smaller goals (like 10-15 pounds at a time).

Every pound lost means using 3500 more calories than you take in. Exercise helps burn the calories and gets you to your goal faster.

FIG-2A

HOME · WHY Sensei · ARTICLES · RECIPES · HEALTH TOOLS · FAQ · About Sensei · JOIN          MY Sensei.com (login)

Sensei CHANGING MINDSETS WITH HANDSETS

Join Sensei

Step 2
Account Details

You know the drill. Fill in the blanks.

Pick a username and password.

We'll send you a confirmation by email.

Your credit card will be charged monthly for the term of your Sensei contract. You can cancel at any time by contacting customer support.

Choose a username (8 chars limit) Check username availability
[_____] — 202

Choose a password
[_____]

Confirm your password
[_____] — 204

Email address
[_____]

Security Question
[_____]

Security Answer
[_____]

First Name
[_____]

Last Name
[_____]

Street Address
[_____]

City
[_____]

State
Choose: [v]

Zip Code
[_____]

Country
United States [v]

FROM FIG-2B1

Birthdate
Month ▽ Date ▽ Year ▽

Mobile Number (xxx-xxxxxx) — 206

Phone (xxx-xxxxxx)

Mobile Model ▽

Mobile Manufacturer ▽

Mobile Carrier ▽

☐ I have read and agree to the Terms of Use.
☐ I have read and agree to the Medical Disclaimer.

Submit ▷

FIG-2B2 mySensei CHANGING MINDSETS WITH HANDSETS

My Diet Plan                              Hello
                                   SIGN OUT | ACCOUNT SETTINGS Your life needs balance. Your diet needs balance.

Balance, portion control, and increased activity are the core of healthy living. Each plan is a balanced approach to nutrition providing some variations in taste and interests.

All the Sensei's meal plans are healthy, will help you lose weight, and keep it off for a lifetime.

Choose the plan that fits your life Remember:
Extremes like starvation or deprivation aren't successful or healthy.
Starvation leads to hibernation, slows your metabolism, and slows your weight loss. Avoiding carbs or fats will only make you crave them more.

SENSEI SENSEIBLE/BALANCE PLAN  → CHOOSE
- Reduces calories by cutting down fat and sugar
- Includes a variety of foods (such as fruits, vegetables, and grain)
- Convenience foods easily fit into this plan
- Based on 2005 Dietary Guidelines

MORE...

SENSEI HEALTHY CARB PLAN  → CHOOSE
- A healthier version of popular low carb diets
- Includes more lean meat, fish, dairy, nuts
- Decreases less healthy carbs and keeps good ones
- Limits sweets and baked goods
- Convenience foods fit into this diet plan

MORE...

SENSEI MEDITERRANEAN PLAN  → CHOOSE
- Includes fish, grains, fruits, vegetables, beans and nuts
- Major fat is olive oil (monounsaturated) and other unsaturated fats
- Some convenience foods may not fit
- Some meals can require a little more preparation time for some meals (but we do have Quick & Easy choices too)

MORE...

208

FIG-2C mySensei CHANGING MINDSETS WITH HANDSETS

Hello
SIGN OUT | ACCOUNT SETTINGS

Food Filter

→ SAVE AND CONTINUE

Don't Send Me These!
We promise not to make you eat foods you don't like. Check off the foods that you avoid and we'll keep them out of your menus. Click the box to select a whole food category or click the icon to expand the list and pick certain foods in each group.

☒ – Category fully selected   ☑ – Category partially selected
☐ – Category empty ☒ Meat, Poultry and Fish ☐ Grains & Soy Products ☐ Vegetables ☑ Condiments and Dressings ☑ Beans, Nuts and Seeds ☐ Fruit ☐ Dairy Other Foods or Dishes Don't see something you're looking for? Type the first letters in a box below and a list of choices will come up. Click the one you want and we'll take that off your menus.

FIG-2D

*mySensei* CHANGING MINDSETS WITH HANDSETS

Hello
SIGN OUT | ACCOUNT SETTINGS

Meal Times

Menu's ready!
You'll have 3 meals and 1 snack on the Sensei program. Schedule your meals every 4-5 hours so you don't go too long without eating.

You will hear from us about 1/2 hour before your meals and snacks.

→ SAVE AND CONTINUE

|  | Weekdays | | | Weekends | | |
|---|---|---|---|---|---|---|
| Breakfast | 7 ⌄ | :30 ⌄ | AM ⌄ | 8 ⌄ | :00 ⌄ | AM ⌄ |
| Lunch | 12 ⌄ | :15 ⌄ | PM ⌄ | 12 ⌄ | :00 ⌄ | PM ⌄ |
| Dinner | 6 ⌄ | :30 ⌄ | PM ⌄ | 6 ⌄ | :30 ⌄ | PM ⌄ |
| Snack | 10 ⌄ | :00 ⌄ | PM ⌄ | 10 ⌄ | :00 ⌄ | PM ⌄ |

→ SAVE AND CONTINUE

My Behaviors

Changing old habits is HARD! If it was easy, we'd all be fabulously thin! Weight loss isn't just about food, and eating isn't always about hunger. Sensei goes beyond the typical diet plan to focus on eating habits you'd like to change. Habits are behaviors we learn through repetition. To change them requires focus, determination, and repetition of positive behaviors. Think of some challenges you might have, and let's work on them together to build positive habits.

→ SAVE AND CONTINUE

My Biggest challenges in healthy eating is that I have always...(Choose 3) — 220

- ☐ Eating when I am stressed
- ☑ Eating in front of the television or when I use the computer
- ☐ Snacking late at night
- ☐ Being an emotional eater (happy and/or sad)
- ☐ Eating when I am bored or don't have things to do
- ☑ Eating too many sweets/snacks at work
- ☑ Being tempted to eat food when it is just there, even if I am not hungry
- ☐

Of your challenges, pick one to work on first — 222

- ◉ Being tempted to eat food when it is just there, even if I am not hungry
- ○ Eating too many sweets/snacks at work
- ○ Eating in front of the television or when I use the computer

FROM FIG-2G1

224

Here are a list of strategies to help you. Pick 1 that fits your lifestyle best

○ Reach for some sugar-free gum to keep your mouth busy without calories
○ Keep snacks in hard to reach places like the top shelf of the cupboard, behind the paper towels
○ Boredom=snacking. Get busy
○ Out of sight, out of mind. Keep hard to resist foods out of the house! If you have to snack, at least let it be healthy.
○ Exercise! Activity is the healthiest way to occupy your time
○ Call a friend and spend time catching up
○ Don't leave food on display–that can trigger an urge.
○ Keep a sugar-free drink handy, staying hydrated can help manage an urge to munch
○ Distract your attention by doing a chore–if at home, clean 1 room in the house
● Head outside for a walk to clear your head and refocus on something other than food

FIG-2G2

Jane Smith, we're ready to help you reach your weight goal of 130lbs.

Nutrition

Your diet plan:

SENSEI SENSEIBLE/BALANCE PLAN

Your food filter:
> Meat, Poultry and Fish
> Nuts & Seeds (all)
> Olives

Your meal preparations:

| | Breakfast | Lunch | Dinner |
|---|---|---|---|
| Weekdays | | | |
| Weekends | | | |

Fitness

Exercise is one of the most powerful things you can do for your health. It's a no-brainer; regular activity along with a healthy diet is the best way to lose weight and maintain it for the long haul.

It's great that you're already doing some exercise. Based on what you told us, we've put together the following exercise program to help you improve your fitness level:

Cardiovascular activities:

| Bicycling | Walking |
|---|---|

Days of activity:

Over time, we will help you increase your duration and frequency so you are doing more.

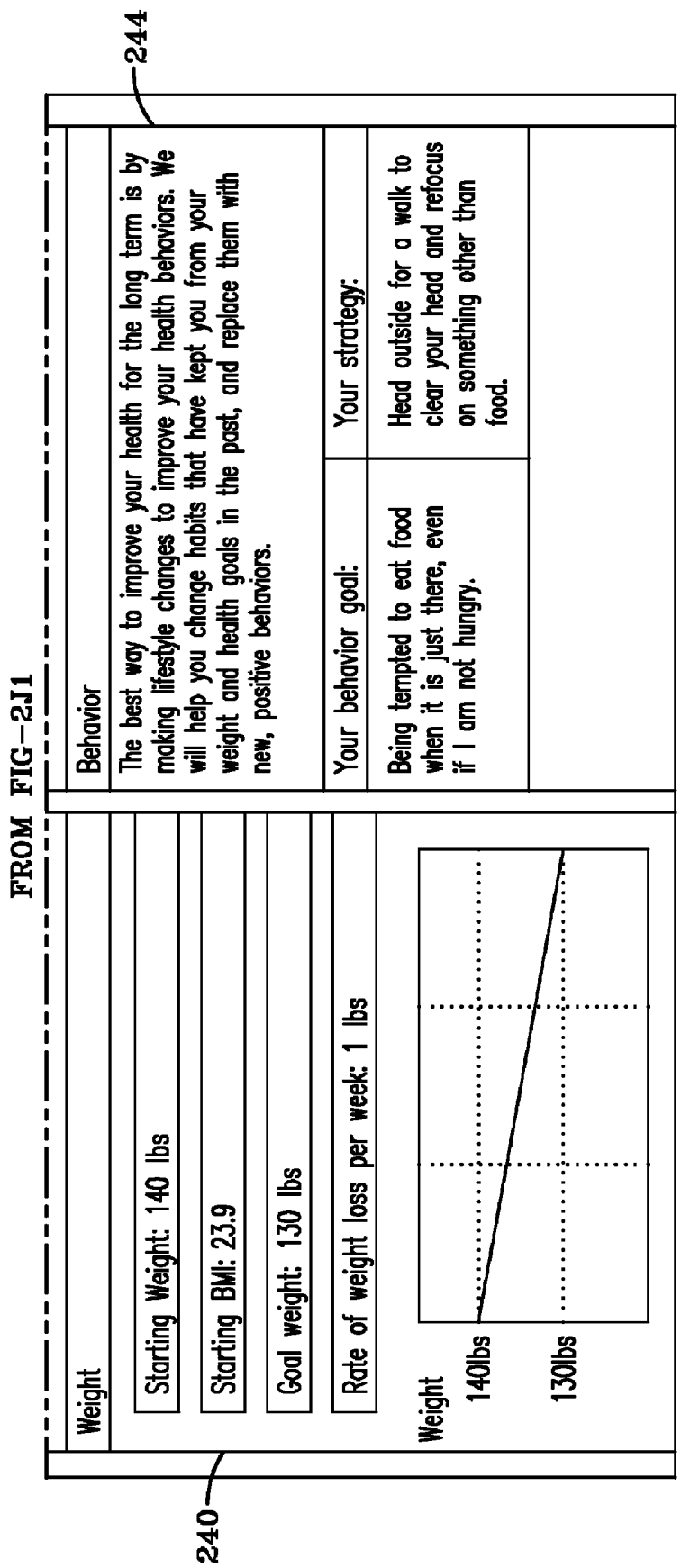
FIG-2J2

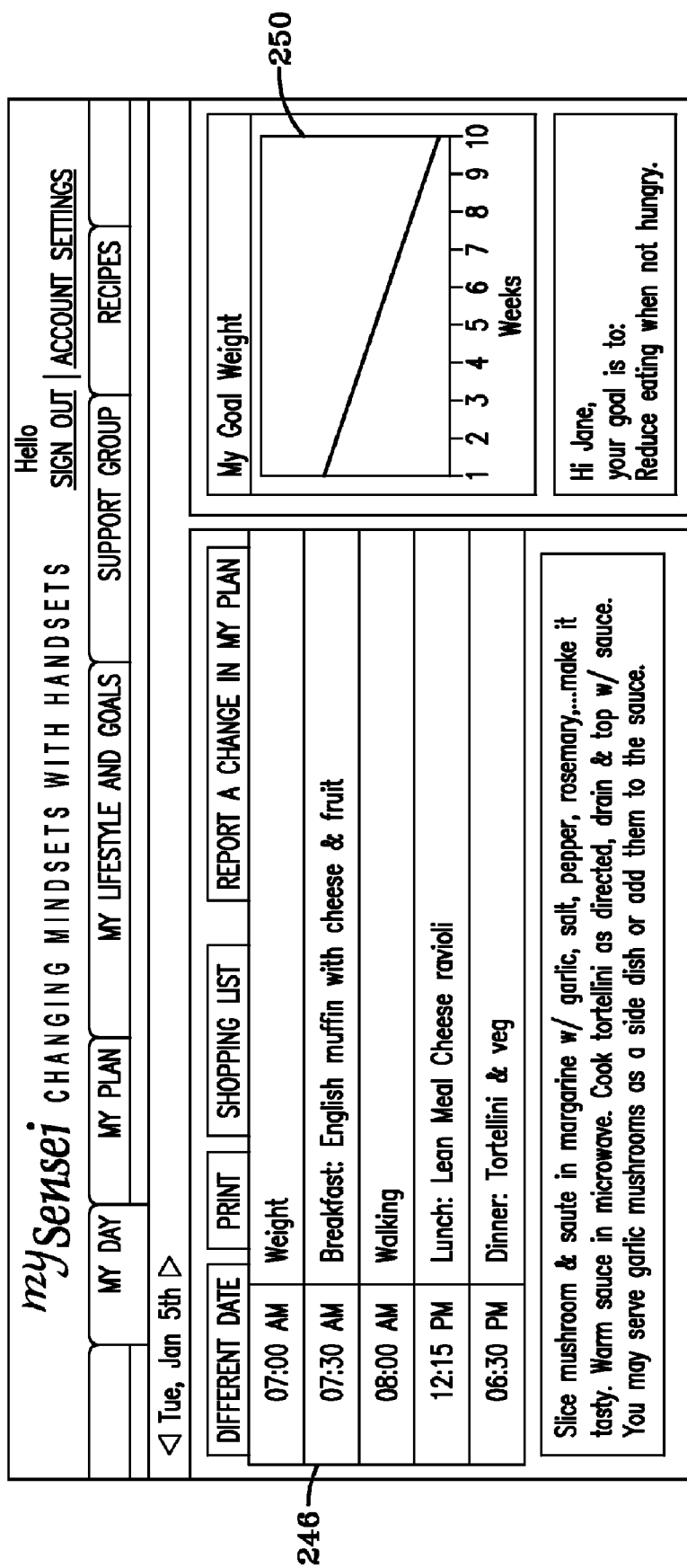
FIG-2K1

FROM FIG-2K1

Click on any ingredient for info and substitutions

1 Cup Cheese tortellini (332kcal)

0.5 Cup Spaghetti sauce cnd (60kcal)

1 Each Portabella mushroom, fresh (27kcal)

1 Teaspoon Margarine red. cal (50cal/Tbsp) (17kcal)

CHANGE THIS MEAL

Total meal calories: 436 calories

| 10:00 PM | Snack: Papaya |

Total day calories: 1200 calories

248

Today's Tip

Put a picture on the fridge of something that motivates you... your children, a thinner you, friends...you decide.

From Sensei Library

Dieting Does Not Equal Deprivation

Do you feel deprived every time you start a diet? That might be one of the reasons that diets don't last!

Check our blog: Sensei Thoughts.

Here is where the Sensei team will share thoughts on what's happening in the world of health and wellness.

New In My Groups

FIG-2K2

*mySensei* CHANGING MINDSETS WITH HANDSETS

Hello
SIGN OUT | ACCOUNT SETTINGS

| MY DAY | MY PLAN | MY LIFESTYLE AND GOALS | SUPPORT GROUP | RECIPES |

MY DIET | MY FITNESS | MY FOOD PREFERENCES

My Diet Plan

| My Plan | CHANGE PLAN | MON | TUE | WED | THU | FRI | SAT | SUN | PRINT MY DIET PLAN — 252 |
|---|---|---|---|---|---|---|---|---|---|
| SENSEI SENSEIBLE/ BALANCE PLAN | | 07:30 AM | | Breakfast: English muffin with cheese and fruit | | | | | |
| | | 12:15 PM | | Lunch: Lean meal Cheese ravioli | | | | | |
| | | 06:30 PM | | Dinner: Tortellini & veg | | | | | |
| | | 10:00 PM | | Snack: Papaya | | | | | |

Your Guidelines

Reduces calories by cutting down fat and sugar.
Includes a variety of foods (such as fruits, vegetables, grain).
Convenience foods easily fit into this plan.
Based on 2005 Dietary Guidelines.

FIG-2L

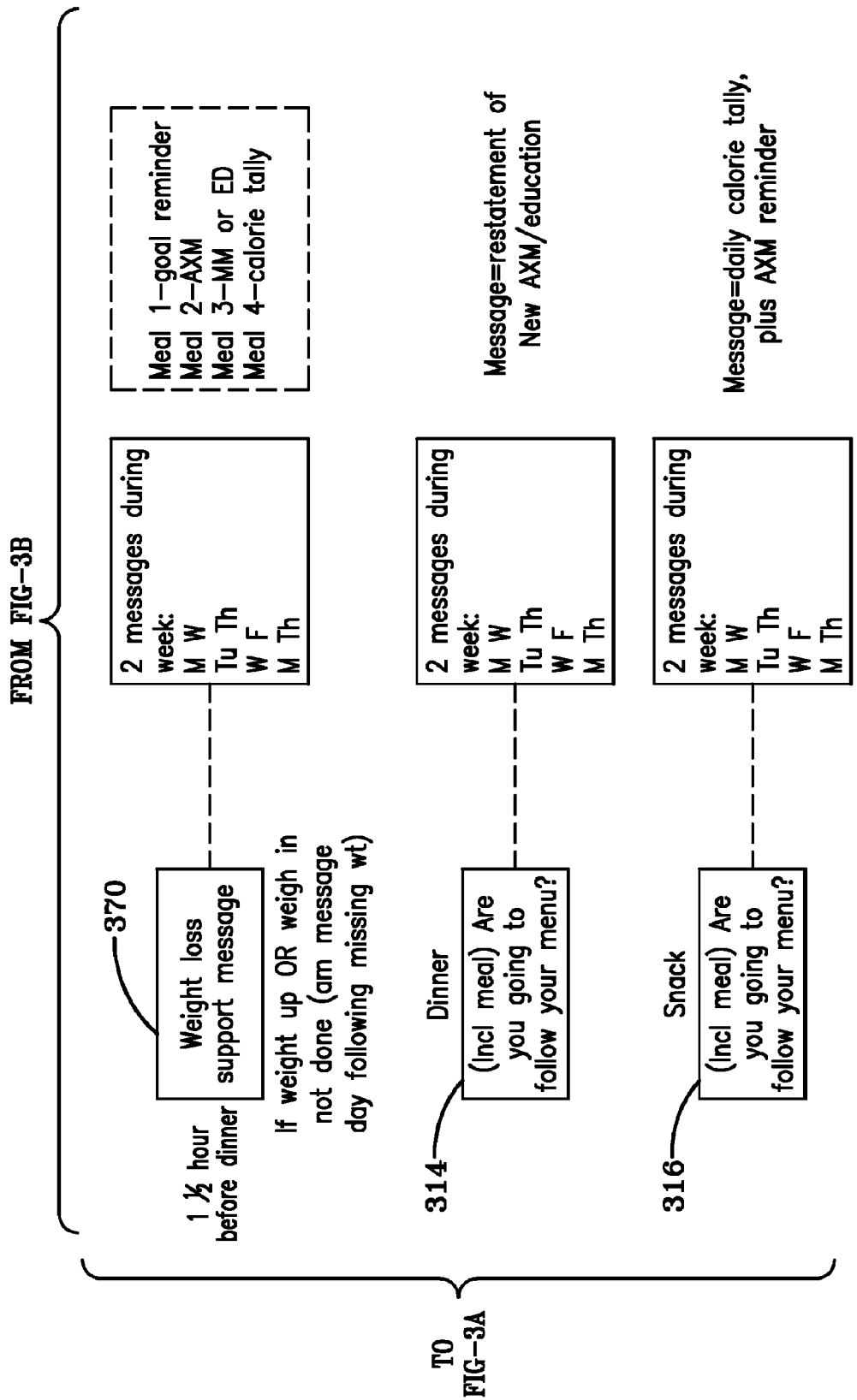

METHOD AND SYSTEM FOR SUGGESTING MEALS BASED ON TASTES AND PREFERENCES OF INDIVIDUAL USERS

CROSS-REFERENCE TO RELATED APPLICATIONS

This application is a continuation-in-part application of U.S. patent application Ser. No. 12/117,190, filed May 8, 2008, titled METHOD FOR TAILORING STRATEGY MESSAGES FROM AN EXPERT SYSTEM TO ENHANCE SUCCESS WITH MODIFICATIONS TO HEALTH BEHAVIORS, which is incorporated herein by reference and is a continuation-in-part application of U.S. patent application Ser. No. 11/856,917 filed Sep. 18, 2007 titled SYSTEM AND METHOD FOR REWARDING USERS FOR CHANGES IN HEALTH BEHAVIORS, which is incorporated herein by reference.

TECHNICAL FIELD

The present invention relates to a system and method for assisting with the maintenance of healthy lifestyle habits. More particularly, the present invention is a system and method for assisting with the maintenance of a healthy diet by pushing meal suggestions from an expert system to individual users wherein the meal suggestions are generated using the personal preferences of the system users both individually and collectively.

BACKGROUND OF THE INVENTION

Many people are affected by a variety of health problems including obesity, diabetes, high blood pressure, and elevated cholesterol levels which can be linked to poor habits in diet, exercise, and the like. Although people are generally aware that controlling diet, exercise, and similar lifestyle habits is the easiest way to become or stay healthy, getting them to adopt and maintain these habits is a difficult task. Many people do not have access to information or to systems or methods that can effectively assist them in these challenging endeavors.

There are many well-known diet and exercise regimes. When using these known regimes, however, individuals must determine what to eat and when to eat as well as calculate the calories they have consumed (e.g., by determining the calorie count of all foods or adding points that are tied to the calorie counts of certain foods) and they must keep an exercise record and determine the caloric impact of their exercise on their overall regime. Another problem with current diet and exercise regimes is that they restrict severely the types of food individuals can consume or the types of activities in which they are guided to participate. This lack of variety causes individuals to become frustrated with their regimes and to give up before they have experienced their desired results.

There are a few known methods and systems for assisting individuals with the maintenance of healthy lifestyle habits, but these methods and systems are expensive and often inaccessible to most people. For example, a highly effective method for assisting individuals in developing and maintaining healthy lifestyle habits is found through the use of coaching. Research has shown that individuals are more successful in the difficult endeavor of changing their habits and maintaining new, healthier ones when they are coached throughout the process. Coaching keeps individuals motivated, provides positive reinforcement, and introduces a narrowly-tailored plan for each individual participant. However, obtaining a reliable human coach is difficult and often prohibitively expensive such that relatively few individuals are actually able to use one. In addition to purchasing the services of a human coach, it has been shown that the services of a personal chef, who is trained in preparing healthy meals, and/or those of a nutritionist, who is able to develop a personalized diet plan, are successful methods for an individual to be assisted in maintaining healthy lifestyle habits, but these methods are also expensive and thus inaccessible to many.

In an attempt to make the services of coaches, nutritionists, personal chefs, and the like accessible to those who could not afford them otherwise, many books have been written and/or home videos produced that focus on disseminating the type of expert information these individuals typically offer their clients. Unfortunately, those who invest in these books and/or videos are noticeably less likely to maintain the healthy lifestyle habits they aim to encourage than those who invest in the actual expert services. The mass marketed materials are aimed at a wide audience and cannot meet the needs of each individual purchaser. The difference that actual health and fitness experts can provide is the ability to provide their clients with appropriate plans and strategy messages with modifications tailored to the individual thereby reducing or eliminating the various barriers to success.

In light of these foregoing problems with known systems and methods, there is a need for a generally affordable and accessible system and method that assists in the maintenance of healthy lifestyle habits by providing individual users with a diet and exercise regime specifically tailored around their personal preferences so that they are not restricted to the point that they become frustrated thus discontinuing their practice of the regime's healthy habits. Additionally, there is a need for a system and method that assists individual users in determining what foods they should be eating, when they should be eating, and/or in what activities they should be participating. The system and method should account for an individual user's preferences, including preferences for meal preparation. Furthermore, the system and method should provide individual users with personalized guidance and strategy similar to that which can be provided by health and fitness experts in order to maximize the probability that individuals will successfully maintain healthy lifestyle habits.

SUMMARY OF THE INVENTIVE CONCEPT

The present invention is a system and method for assisting with the maintenance of healthy lifestyle habits by generating meal suggestion messages using an expert system and then pushing those suggestions to individual users. The system and method allow diet plans to be tailored to individual users based on their preferences and provides consistent and appropriate strategy messages including meal suggestions designed to encourage and motivate users toward successfully maintaining healthy lifestyle habits. The system and method utilizes modern technologies, such as the cellular phone or other portable device, to facilitate the pushing of the tailored messages from the system's computer-based expert system to the individual users.

Individual users complete initial assessments that detail each individual's food and physical activity preferences. These assessments are then used to compile profiles for each individual that are stored in a database. The system and method use the profile information in the database to generate individualized messages that are pushed to individual users through a system incorporating cellular technologies. Tailored meal suggestion messages are pushed from a computer based expert system to an individual user's cell phone at predetermined times each day. The message generated by the computer-based expert system provides an individual user with a healthy suggestion for his or her next meal based on the type of food he or she indicated to have preferred as well as the preferred preparation option designated when completing the initial assessment.

The system and method can be interactive and an individual user can respond to meal suggestions by either accepting or rejecting the suggestions with a reply message. The computer-based expert system analyzes reply messages generated by individual users. For example, if an individual user indicates a desire to reject a given suggestion in a reply message, the computer-based expert system detects that desire through analysis and generates a new message for the user that contains a different suggestion designed to replace that which the user had previously rejected. Likewise, if an individual user indicates in a reply message a desire to accept a given suggestion, the computer-based expert system detects that desire through analysis of the reply.

The system can use information regarding accepted and rejected suggestions for a variety of purposes. For example, if the system detects an individual user consistently rejects suggestions to eat a certain meal the system will cease to generate such suggestions for the individual. Additionally, if the system detects that the majority of its users consistently reject suggestions to eat a certain meal the system will cease to generate such suggestions for all users. The system can track separate ingredients that individual users tend to incorporate into their meals as well as those that individual users tend to reject. The system can use the records of ingredient acceptance and rejection as a means of determining if and when certain ingredients should no longer be recommended to individual users or to system users as a whole. By tracking meals and separate ingredients that have consistently been accepted and rejected by its users, the expert system is able to make meal suggestions for its users that they will likely enjoy. When individual users are satisfied with the foods they are eating, they are more likely to follow the plan and reach their diet and exercise goals.

The system and method also tracks the actions and progress of individual users. For example, if an individual user desires to lose weight, the system monitors the food the individual consumes to determine the impact of the meals on the individual's goal. The monitoring function and updating of information in the database helps to ensure that the system sends messages that are appropriate for each individual user as their habits and/or preferences change and as they progress toward a goal. The system generates messages praising users as they attain their goals and provides motivational messages to users that stray from their goals. The system also assists users with formulating new goals as well as strategies as may be needed.

The system and method is both affordable and accessible to many users because it is operated via applications to prevalent and relatively inexpensive modern technologies. The system and method addresses problems inherent in the prior art and makes the key to good health accessible in an original and novel way.

BRIEF DESCRIPTION OF THE DRAWINGS

FIG. 2A-2L are screen shots for completing a user profile and specifying preferences according to an example embodiment;

DETAILED DESCRIPTION

One exemplary embodiment is a "smart system" designed to encourage and motivate users towards successfully maintaining healthy lifestyle habits by pushing tailored meal suggestion messages from a computer based expert system to individual users via cellular technologies. The system incorporates the personal preferences of individual users in regard to diet, exercise, and other similar habits in conjunction with personal information such as age, weight, gender, and desired results as well as behavioral challenges in order to generate tailored messages to assist individual users with the adoption and maintenance of healthy lifestyle habits.

Figure 1:
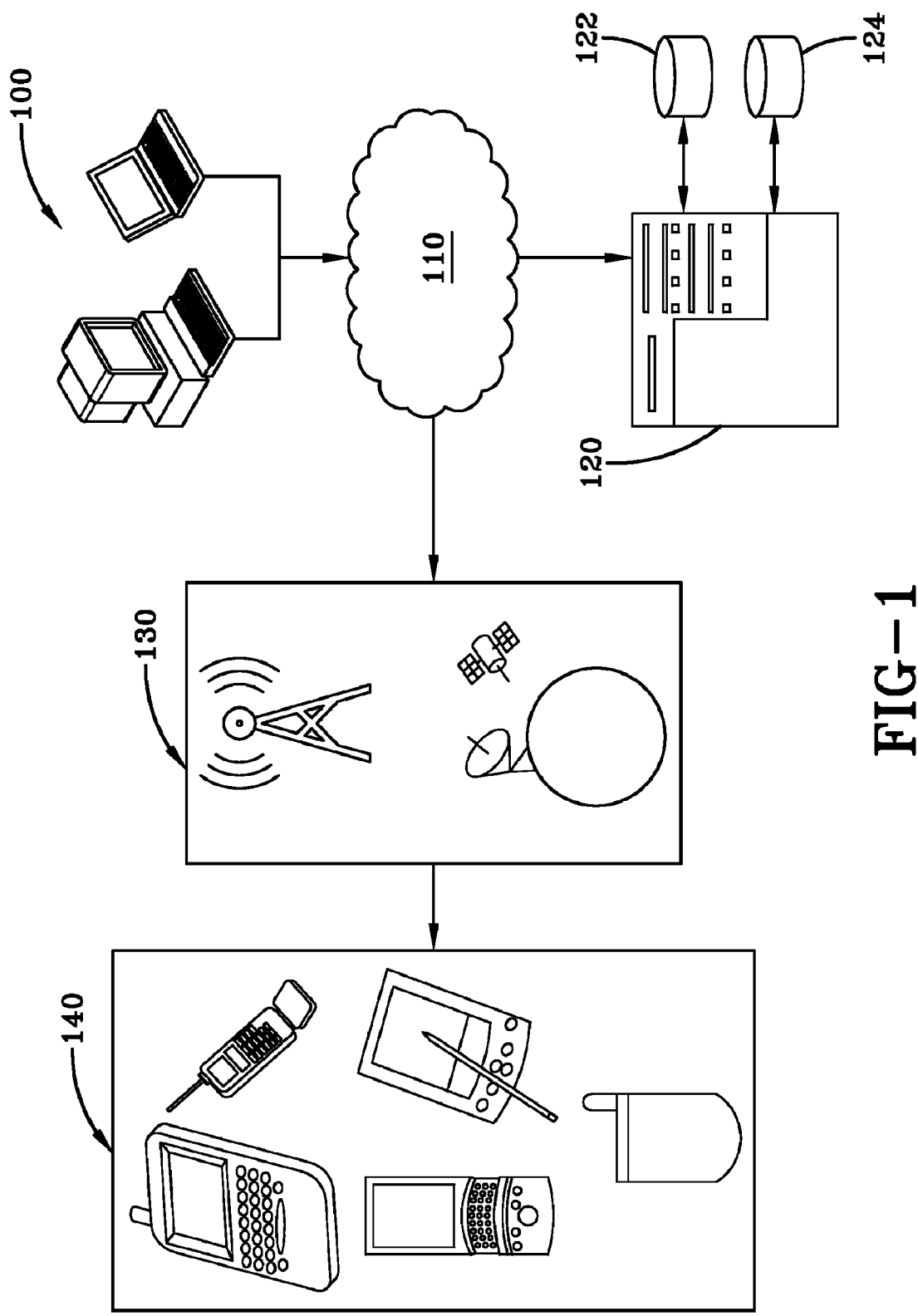
FIG. 1 illustrates the physical structure of a system according to an example embodiment.

FIG. 1 shows one embodiment of the physical structure of the system. Each of the connections mentioned here permit data to flow in both directions. A laptop or desktop personal computer 100 is connected to the server 120 through the internet 110. The user may connect to a website to create an account and enter personal information and preferences for creating a profile. The server 120 is connected to one or more databases 122, 124 comprising user data, nutrition provider data (nutritional data related to meals offered by a plurality of meal providers), diet, and exercise data, message data, progress data, compliance data, restaurant, shopping, and entertainment establishment data, reward data, and other data as may be required to provide the features and functionality of the present invention. The server 120 is connected to communication networks 130 (comprising various data transmitters and receivers) through the internet 110. The various data transmitters and receivers of the communication networks 130 facilitate communications with the user's portable technology 140 which includes cellular or mobile phones, personal digital assistants, or any other portable device capable of sending and receiving communications through the communication networks 130 and displaying them for a user. An expert system at the server uses the individual's account information, including information about the individual's mobile phone, to tailor and send to the individual messages to reinforce and motivate healthy habits.

In an example embodiment, the expert system is constructed using the J2EE programming language in conjunction with a SQL based database (like Microsoft SQL Server or Oracle DB). AJAX, Active X, and Java components may also be used to handle various aspects of the system. The mobile component of the overall system is constructed using the J2ME programming language sending wireless requests to the expert system over common carrier communication protocols. Communication between the mobile component and the expert system is constructed using XML language structures.

Referring to FIGS. 2A-2L, screen shots for completing a user profile, specifying diet and exercise preferences, and identifying health behavioral challenges in an enrollment process according to an example embodiment are shown. The user provides contact and background information, specifies a weight goal, specifies preferences related to diet and exercise, and identifies personal behavioral challenges. The user's profile data and specified goal and diet and exercise preferences are considered by the expert system to tailor messages. The user accesses a website to navigate through the screens and provide data and information that allows the system to build a profile for the user comprising diet and exercise preferences as well as behavioral challenges.

Referring to FIG. 2A, a screen for specifying physical characteristics and a weight goal is shown. The user specifies a sex, age, weight, and height and a goal weight 200. This information is saved in the user's profile and used to determine the user's progress toward the goal. The expert system generates tailored messages that help the user to progress toward the specified goal.

Referring to FIG. 2B, an account screen for an example embodiment is shown. First, as shown in FIG. 2B1, the user specifies a username, password, and email address to create an account 202. Next, the user provides contact information 204. The user also provides information about his or her mobile phone or other portable device so that messages from the expert system can be pushed to the portable device 206 as shown in FIG. 2B2.

Referring to FIG. 2C, a diet plan screen for an example embodiment is shown. The user specifies the type of diet plan he or she would like to follow. In an example embodiment, the user may select from one of three diet plans 208. A first plan is a balanced plan that emphasizes a diet of reduced calories as well as reduced fat and sugar. A second plan is a healthy carbohydrate plan that emphasizes a diet of lean meats, fish, dairy, and nuts. A third plan is a Mediterranean plan that emphasizes a diet of fish, grains, fruits, vegetables, beans, and nuts.

Referring to FIG. 2D, a food preference screen for an example embodiment is shown. The user selects a food category and identifies the foods in each category that he or she does not like or wants to avoid 210. In an example embodiment, the categories include: 1) meats, poultry, and fish; 2) beans, nuts, and seeds; 3) grains and soy products; 4) fruit; 5) vegetables; 6) dairy; and 7) condiments and dressings. Within each category, the user can select from a list the foods he or she does not want to eat. Alternatively, an entire category of food can be selected. Finally, if the user does not find a particular food on any list within a category, the specific food can be entered in a text box 212. As the user types, choices matching the entered text are presented. Foods identified in the text boxes as well as foods selected from the category lists are not included in any menu or meal suggestions that are provided to the user.

Figure 2F:

Referring to FIG. 2E, a meal times screen according to an example embodiment is shown. The user specifies a time of day for eating breakfast, lunch, and dinner as well as a snack 214. The user specifies two sets of meal times, one for weekdays and one for weekends. Referring to FIG. 2F, a meal preparation preference screen according to an example embodiment is shown. On this screen, the user specifies preferences related to meal preparation options 216. Using a drag and drop feature, the user specifies meal preparation preferences for breakfast, lunch, and dinner on weekdays and weekends 218. In an example embodiment, the meal preparation options are: 1) quick and easy (fewer than 10 minutes to prepare); 2) cook at home (more than 10 minutes to prepare); 3) frozen or ready to eat; 4) fast food; or 5) order from restaurant. The meal preparation preferences provide additional data for the expert system to consider when generating messages to the user related to meal suggestions.

Referring to FIG. 2G, a behavior challenges screen according to an example embodiment is shown. The screen in FIG. 2G1 presents common challenges to a healthy lifestyle 220 and allows the user to select the ones that are applicable. The user is also asked to identify the challenge he or she would like to overcome first (a priority challenge) 222. Finally, the screen presents a list of strategies for overcoming common challenges 224 as shown in FIG. 2G2. The user is asked to select a strategy that is appropriate for the user's lifestyle. The user's selections related to applicable challenges, a priority challenge, and a challenge strategy are considered by the expert system in generating tailored messages.

Figure 2H:
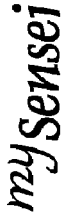
Figure 2I:
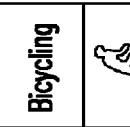

Referring to FIG. 2H, an activity screen according to an example embodiment is shown. The user provides information about his or her current activity level 226 and exercise frequency 228. In addition, the user indicates whether he or she smokes 230. The user's selections related to current activity level, exercise frequency, and smoking are considered by the expert system in generating tailored messages. Referring to FIG. 2I, a workout screen according to an example embodiment is shown. Using a drag and drop feature, the user identifies preferred physical activities 232 and specifies times for performing the physical activities on a weekly basis 234. The preferences related to physical activities and times are considered by the expert system in generating tailored messages.

Referring to FIG. 2J, a profile overview screen according to an example embodiment is shown. The screen in FIG. 2J1 presents information regarding the data and preferences specified by the user while completing the profile data entry screens. A nutrition section comprises the user's selections related to a diet plan and specific food preferences 236 as well as meal preparation preferences 238. A weight section comprises the user's personal data related to current weight and body mass index as well as goal weight and proposed rate of weight loss per week 240 as shown in FIG. 2J2. A fitness section comprises the user's selections related to physical activity preferences 242 as shown in FIG. 2J1. A behavior section comprises information about the user's priority challenge and preferred strategy from overcoming the challenges he or she specified previously 244 as shown in FIG. 2J2.

Referring to FIG. 2K, a daily plan screen according to an example embodiment is shown. The daily plan screen as shown in FIG. 2K1 presents a complete schedule of activities and meal suggestions based on the personal data and preferences specified by the user previously 246. In the example schedule, the user takes a weight reading at 7:00 AM, eats the suggested breakfast at 7:30 AM, completes the suggested activity at 8:00 AM, and eats the suggested lunch and dinner at the specified times. The daily plan screen also presents food substitution suggestions in the event the user does not want to follow the initial meal suggestion 248 as shown in FIG. 2K2. The user can select any ingredient in the specified meal suggestion and select a substitution. The ability to substitute ingredients in a specified meal allows the user change the meal only slightly or to change the entire meal to meet his or her preferences at mealtime. Finally, the screen may display a goal weight 250 as shown in FIG. 2K1. Referring to FIG. 2L, a diet plan screen according to an example embodiment is shown. At this screen, the user can review the weekly meal suggestions 252 and complete any substitutions prior to receiving the meal suggestions on at the mobile phone or other portable device.

Figure 3A:
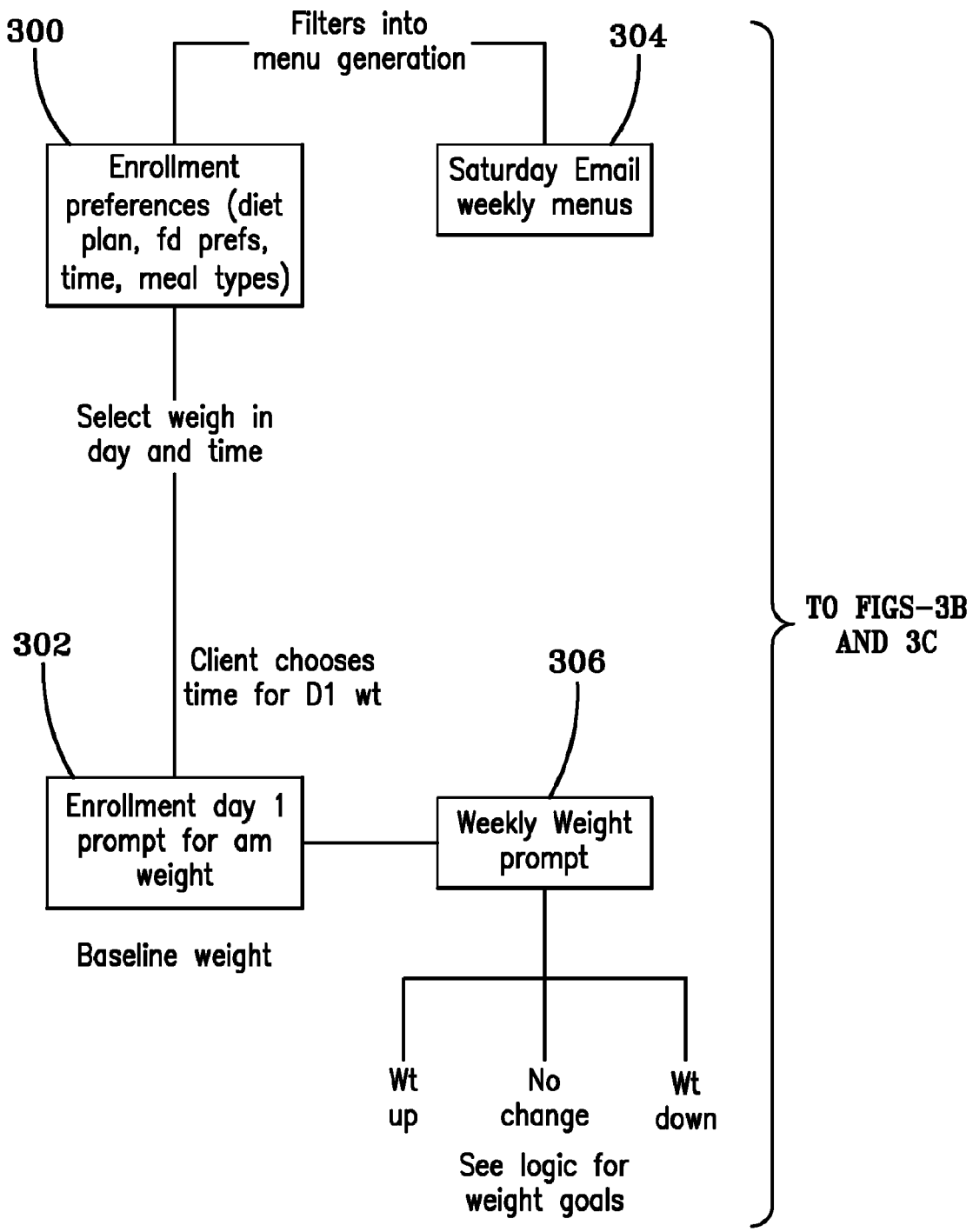
FIG. 3 is meal contact logic according to an example embodiment.

Referring to FIG. 3, meal contact logic according to an example embodiment is shown. Referring to FIG. 3A, the user's specified preferences 300 and enrollment weight 302 are considered by the computer based expert system in generating meal suggestions. The user's specified preferences 300 (provided during enrollment) include an individual user's diet plan, food preferences, meal times, meal preparation selections, etc. The starting or enrollment weight 302 is the weight entered by the user at enrollment when he or she starting using the system. Once the computer based expert system has generated menus for an individual user according to preferences, a weekly menu message 304 is pushed to the user. Because of the size of the message, the weekly menu message is emailed from the computer based expert system to the individual user. It could also be delivered via a text message to an individual user's cell phone, etc. A user may also receive a weekly weight prompt message 306 for reporting any weight change during the previous week.

Figure 3B:
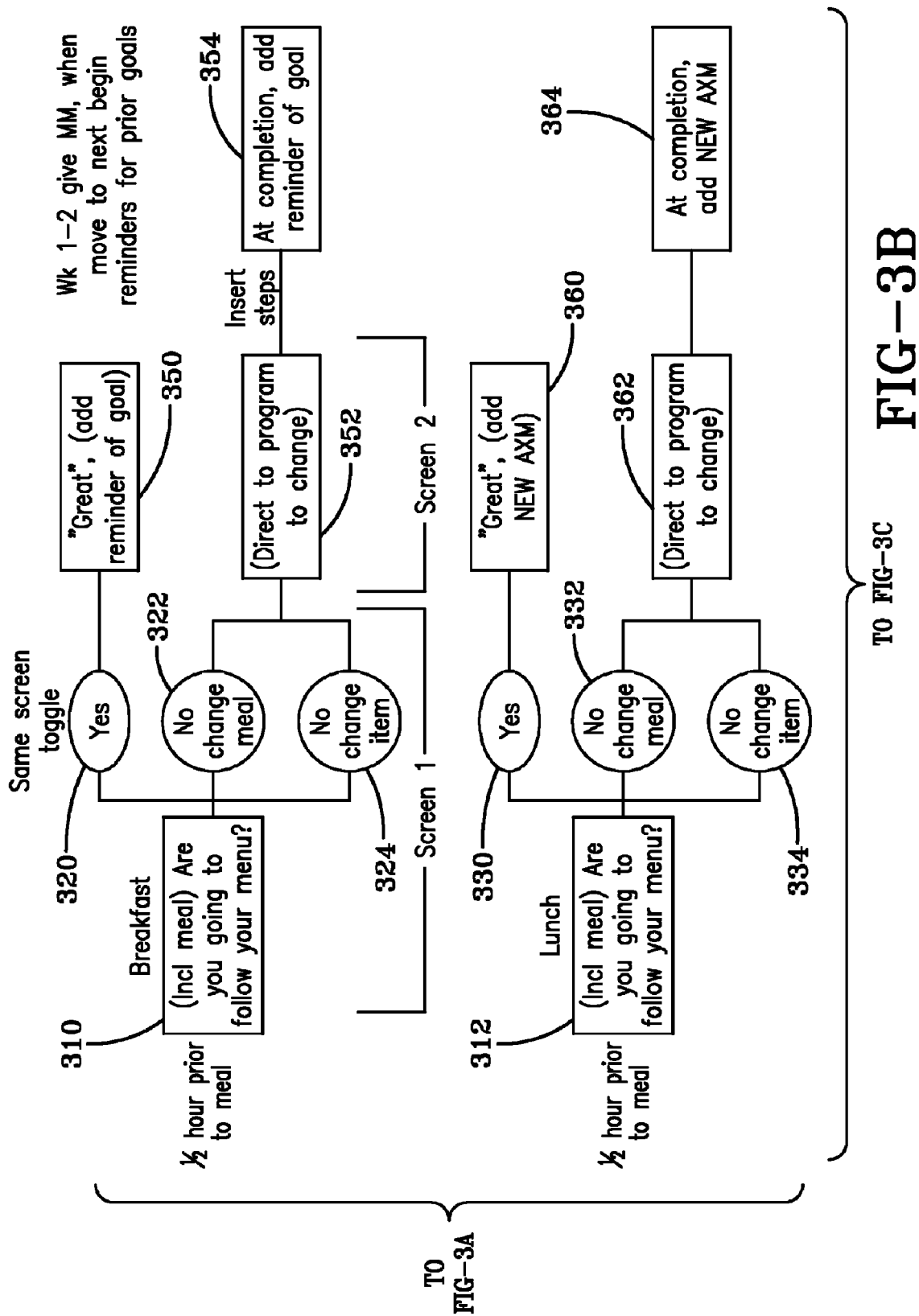

As shown in FIG. 3B, the meal contact logic of the system and method uses daily phone contacts 310 through 316 that are sent to an individual user before he or she eats a meal. The daily phone contacts 310 through 316 are sent approximately thirty minutes before a scheduled meal. The daily contact breakfast message 310 asks the user to indicate whether he or she is going to eat the suggested breakfast (e.g., from an earlier received weekly menu message). The responses include a "Yes" response 320 indicating the user plans to eat the suggested meal, a "No change meal" response 322 indicating the user would like an entirely different meal, or a "No change item" response 324 indicating the user would like to substitute one or more items in the suggested meal. If the user selected the "yes" response, a positive message and reminder of the user's goal is sent 350. If the user selects either "no" response 322, 324, the expert system accesses a database of meal and menu substitutions and suggests either an entirely new meal or one or more food substitutions 352. The new suggestions conform to the user's food preferences and meal preparation preferences as well as dietary needs for meeting the target goal. A reminder message for the user's goal is also sent 354.

Similar logic applies to the user's lunch 312 as well as dinner 314 and a snack 316. The user is asked whether he or she intends to follow the plan 330 or whether he or she would like a different meal 332 or different items in the meal 334. If the user follows the suggestion, a positive message is sent 360 and if the user changes the meal, new suggestions consistent with the user's preferences are sent 362. At completion, an AXM? Message is sent to the user 364. The daily phone contacts 310 through 316 can be used to remind an individual user what foods he or she needs to be eating to reach the desired goal.

As shown in FIG. 3C a weight loss support message 370 may be sent from the computer based expert system to an individual user. The message may be sent twice a week, ninety minutes before dinner. A weight loss support message may remind the user of the week's progress toward the goal, provide the user with tips on what he or she might do to increase the likelihood of reaching the goal, etc.

Figure 4:
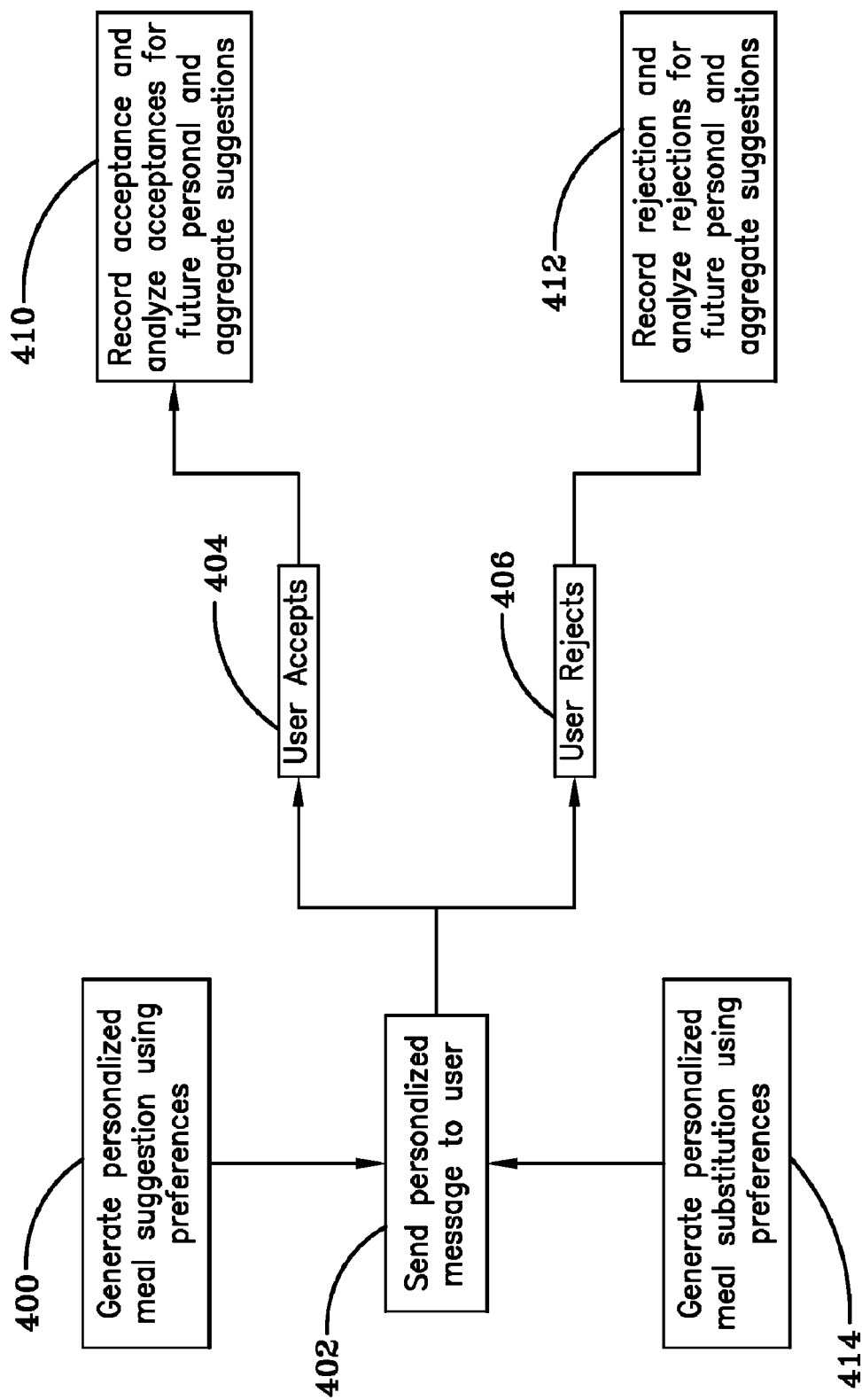
FIG. 4 is suggestion generating logic according to an example embodiment.

Referring to FIG. 4, suggestion generating logic according to an example embodiment is shown. Meal suggestions are generated 400 and sent to user 402 in advance of each meal. Each meal suggestion corresponds to an individual's preferences regarding a diet plan, food preferences, and meal preparation preferences. For example, a user that prefers frozen/ready to eat meals for lunch will receive a lunch time meal suggestion for a frozen or ready to eat meal consistent with the user's selected diet plan as well as food preferences. If the user previously identified a dislike for beef, the meal suggestion will not include a beef entrée.

The positive 404 as well as negative 406 meal suggestion responses of individual users are recorded and analyzed 410, 412 in order to make system adjustments in meal suggestions to be generated in the future. In response to suggestions that a user rejects, the system generates a meal substitution message based on the user's preferences 414. By processing replies to the personalized messages, the system is able to update its database as to the tastes and preferences of each individual user as well as the overall user population. The tracking of separate ingredients as well as complete meals accepted or rejected by users allows the system to alter future meal suggestions based on the recorded tastes and preferences.

Any embodiment may include any of the optional or preferred features of the other embodiments. The exemplary embodiments herein disclosed are not intended to be exhaustive or to unnecessarily limit the scope of the invention. The exemplary embodiments were chosen and described in order to explain the principles so that others skilled in the art may practice the invention. Having shown and described exemplary embodiments, those skilled in the art will realize that many variations and modifications may be made to affect the described invention. Many of those variations and modifications will provide the same result and fall within the spirit of the claimed invention. It is the intention, therefore, to limit the invention only as indicated by the scope of the claims.

The invention claimed is:

1. A computerized method for providing meal suggestions to a user consistent with said user's dietary preferences, comprising:
    (a) receiving at a computer from a user personal and dietary preference data, said personal data comprising contact information and said dietary preference data comprising a diet plan selection, food preferences, meal time preferences, and meal preparation preferences for said user;
    (b) accessing at said computer a computer accessible database comprising dietary and nutritional data for a plurality of foods and recipes to identify foods for a meal consistent with said user's diet plan selection, food preferences, and meal preparation preferences;
    (c) generating at said computer a primary personalized message comprising a meal suggestion for said user, said meal suggestion consistent with said user's diet plan selection, food preferences, and meal preparation preferences;
    (d) determining at said computer a time for sending said computer-generated message consistent with said user's meal time preference for eating said meal;
    (e) automatically sending from said computer to said user's cellular device at said time said computer-generated primary personalized message comprising said meal suggestion message to said user using said contact information;
    (f) receiving at said computer from said user's cellular device a user response to said primary personalized message;
    (g) generating at said computer a secondary personalized message responsive to said user response; and
    (h) automatically sending from said computer to said user's cellular device said computer-generated secondary personalized message.

2. The computerized method of claim 1 wherein
    said user response to said primary personalized message comprising meal suggestion comprises a response selected from the group consisting of:
    an acceptance of said meal suggestion a request to replace said meal suggestion, and a request to modify said meal suggestion.

3. The computerized method of claim 1 wherein receiving at said computer said user response to said meal suggestion comprises receiving a positive response.

4. The computerized method of claim 1 wherein receiving at said computer said user response to said meal suggestion comprises receiving a negative response.

5. The computerized method of claim 4 further comprising:
    (g) generating at said computer a secondary personalized message comprising a meal substitution, said meal substitution message consistent with said user's diet plan selection, food preferences, and meal preparation preferences; and (h) sending from said computer to said user's cellular device said computer-generated secondary personalized comprising meal substitution to said user.

6. The computerized method of claim 5 wherein said meal substitution comprises a suggested substitution for a food item in said meal suggestion.

7. The computerized method of claim 5 wherein said meal substitution comprises a suggested substitution for an entire meal in said meal suggestion.

8. The computerized method of claim 2 further comprising:
(g) recording said user response to said primary personalized message comprising said meal suggestion; and
(h) updating said food preferences for said user based on said user response to said meal suggestion.

9. A computerized system for providing meal suggestions to users consistent with said users' dietary preferences, comprising:
a first computer accessible database comprising personal and dietary preference data for a plurality of users, said personal data for said plurality of users comprising contact data for sending messages to said users and said dietary preference data comprising diet plan selections, food preferences, meal time preferences, and meal preparation preferences for each of said plurality of users;
a second computer accessible database comprising dietary and nutritional data for a plurality of foods and recipes;
a computerized expert system for analyzing dietary preference data for said plurality of users from said first computer accessible database and dietary and nutritional data from said second computer accessible database and for generating meal suggestion messages for each of said plurality of users based on analysis of said diet plan selections, food preferences, and meal preparation preferences for each of said plurality of users and said dietary and nutritional data; and
a server connected to said computerized expert system for:
(a) sending said computer-generated meal suggestion messages to cellular devices said plurality of users, wherein said server sends said meal suggestion messages according to said meal time preferences specified by each of said plurality of users; and
(b) receiving from said cellular devices of said plurality of users acceptance or rejection responses to said meal suggestion messages;
wherein said computerized expert system:
(1) analyzes said acceptance or rejection responses to update said food preferences for said plurality of users; and
(2) generates additional messages for said plurality of users consistent with said updated food preferences for said plurality of users; and
(3) transmits to said cellular devices of plurality of users said additional messages.

10. The computerized system of claim 9 wherein said meal suggestion messages are delivered 15 minutes in advance of each of said plurality of users' preferred meal time.

11. The computerized system of claim 9 wherein said additional meal suggestion messages are meal substitution messages.

12. The computerized system of claim 11 wherein said meal substitution messages comprise suggested substitutions for food items in said meal suggestion messages.

13. The computerized system of claim 11 wherein said meal substitution messages comprise suggested substitutions for entire meals in said meal suggestion messages.

14. The computerized system of claim 11 further comprising a meal suggestions application at said server for use by said users to review a plurality of meal suggestions and to complete modifications to said meal suggestions.

15. A computerized method for providing meal suggestions to a user consistent with said user's dietary preferences which may be altered over time, comprising:
(a) receiving at a computer from a user personal and dietary preference data, said personal data comprising contact information and said dietary preference data comprising a diet plan selection, food preferences, and meal preparation preferences for said user;
(b) accessing at said computer a computer accessible database comprising dietary and nutritional data for a plurality of foods and recipes to identify foods for a meal consistent with said user's diet plan selection, food preferences, and meal preparation preferences;
(c) generating at said computer a meal suggestion message for said user, said meal suggestion message consistent with said user's diet plan selection, food preferences, and meal preparation preferences;
(d) automatically sending from said computer said computer-generated meal suggestion message to a cellular device for said user using said contact information;
(e) receiving at said computer from said cellular device a user rejection to said meal suggestion message;
(f) updating said dietary preference data based said user's rejection of said meal suggestion;
(g) generating a substitution meal suggestion message based on said user's diet plan selection, food preferences, and meal preparation preferences; and
(h) automatically sending from said computer said substitute meal suggestion to said user cellular device.

16. The computerized method of claim 15 wherein:
(i) generating at said computer a substitution meal suggestion message for said user comprises generating a message with substitute ingredients for said meal suggestion.

17. The computerized method of claim 15 further comprising:
(i) generating at said computer a substitution meal suggestion message for said user comprises generating a message substituting all ingredients in said meal suggestion.

18. The computerized method of claim 15 further comprising:
(i) determining at said computer if a plurality of users have rejected an ingredient in said meal suggestion message; and
(j) updating said database comprising dietary and nutritional data to eliminate said ingredient from additional meal suggestion messages sent to said plurality of users.

* * * * *